(12) United States Patent
Holcombe et al.

(10) Patent No.: US 7,194,915 B1
(45) Date of Patent: Mar. 27, 2007

(54) LEVER CONNECTOR TEST FIXTURE

(75) Inventors: Roy M. Holcombe, Plymouth, MI (US); Jen Vun Ng, Westland, MI (US); Bryan D. Cole, Canton, MI (US)

(73) Assignee: Yazaki North America Inc, Canton, MI (US)

( * ) Notice: Subject to any disclaimer, the term of this patent is extended or adjusted under 35 U.S.C. 154(b) by 105 days.

(21) Appl. No.: 11/157,731

(22) Filed: Jun. 21, 2005

(51) Int. Cl.
*G01N 3/08* (2006.01)
*G01N 3/02* (2006.01)
*B23P 19/00* (2006.01)

(52) U.S. Cl. .............................. 73/818; 73/856; 29/796
(58) Field of Classification Search .................. 73/818, 73/856; 29/796, 261
See application file for complete search history.

(56) References Cited

U.S. PATENT DOCUMENTS

| | | | | |
|---|---|---|---|---|
| 2,618,183 A * | 11/1952 | Cooke | .......................... | 29/267 |
| 3,050,841 A * | 8/1962 | Esselstyn | ..................... | 29/268 |
| 3,129,584 A * | 4/1964 | Canning et al. | ....... | 73/862.584 |
| 3,422,521 A * | 1/1969 | Beinhaur | ..................... | 29/764 |
| 3,632,973 A * | 1/1972 | O'Keefe | ..................... | 219/230 |
| 3,896,533 A * | 7/1975 | Ullman et al. | .............. | 227/140 |
| 3,909,899 A * | 10/1975 | Witt | ............................. | 29/764 |
| 4,066,082 A * | 1/1978 | Arcan et al. | ................. | 606/102 |
| 4,068,374 A * | 1/1978 | Coller | .......................... | 29/747 |
| 4,211,108 A * | 7/1980 | Seitz et al. | .............. | 73/862.01 |
| 4,425,704 A * | 1/1984 | Cline | .......................... | 29/764 |
| 4,907,458 A * | 3/1990 | Biggs et al. | .................. | 73/827 |
| 5,195,381 A * | 3/1993 | Keibler | ..................... | 73/862.05 |
| 5,686,670 A * | 11/1997 | Vanderlip | ..................... | 73/827 |
| 5,731,525 A * | 3/1998 | Boe | ............................. | 73/831 |
| 5,823,808 A * | 10/1998 | Clark et al. | ................. | 439/157 |
| 5,876,225 A * | 3/1999 | Katsuma et al. | ............ | 439/157 |
| 6,019,620 A * | 2/2000 | Kodama et al. | ............ | 439/157 |

\* cited by examiner

*Primary Examiner*—Edward Lefkowitz
*Assistant Examiner*—Punam Patel
(74) *Attorney, Agent, or Firm*—Young Basile PC

(57) ABSTRACT

A universally adjustable tool for measuring the force required to throw the lever of a lever-type, two-part, electrical connector. The tool comprises a handle, a base bar to which the handle is slideably attached, and a pair of legs having adaptors to permit the tool to be mounted to the lever pivot of the connector. A load cell adjustably depends from the free end of the handle and is operably connectable to the lever by means of a catch in the form of a hook or other desired shape. Various joints and a slide bracket, along with connector adaptors, provide a universal tool adaptable for use with a wide variety of two-part matable lever type connectors.

13 Claims, 3 Drawing Sheets

LEVER CONNECTOR TEST FIXTURE

FIELD OF THE INVENTION

This invention relates to force measurement tools and more particularly to a tool which can be used to measure the forces required to mate and/or unmate a two-part electrical connector of the type having a lever pivotally mounted on one of the parts and operable to bring the two parts into a fully joined condition.

BACKGROUND

Two-part electrical connectors having angularly movable levers to assist in the mating and demating the two parts are well known. Such electrical connectors are disclosed in U.S. Pat. Nos. 6,019,620, 5,876,225 and 5,823,808. Lever connectors may be loosely assembled into a "preset" condition and thereafter drawn fully together by rotation of a lever attached between two coaxial, spaced pivots on the interior or exterior of one of the two connector parts. The side portions of the lever arm slidingly engage pins on the sides of the other of the two connector parts such that, when the lever is rotated in one direction, it pulls the two connectors together via the pivots and pins. The lever may be angularly displaced in the opposite direction to demate the connector parts.

Although the manufacturing processes for such connectors are carried out with great care, a small percentage of defective connectors may nevertheless be produced. A defect in a lever-type connector frequently shows up as an abnormality in the force required to operate the lever to mate or unmate the two connector parts.

SUMMARY OF THE INVENTION

The present invention, in one aspect, is a tool for precisely measuring the force required to operate a two-part connector of the type having a lever mounted between two spaced coaxial pivots on one of the two connector parts. In general, the tool of the present invention comprises a pair of spaced-apart legs which are adapted to be attached to the connector pivots, a catch, such as a hook, adapted to engage the lever and to exert a force thereon, a load cell attached to the catch to produce a signal related to the force exerted through the catch, and a handle connecting the load cell to the legs, such that angular movement of the handle and legs about the connector pivot axis swings the lever to mate or unmate the connector parts. In other words, the load cell measures the force needed to mate the connectors. The resulting load cell signal can therefore be compared to a predetermined standard force to determine whether or not the operating force of a given connector is within acceptable limits. The comparison may be done automatically or manually.

In the preferred form hereinafter described in detail, the tool is provided with a number of adjustment features whereby the tool may be configured and/or adapted to work with a range of connectors of different configurations and sizes; however, it is to be understood that a tool made in accordance with the invention may also be of fixed configuration such that it may be used only with a given size and configuration of connectors. In either event, it will be apparent to those skilled in the art that the preferred configuration of the tool is such that the force vector applied by the catch is essentially tangential to the displacement arc of the connector lever at all times through the range of movement which is used for measurement purposes.

According to a second aspect of the invention, a method for measuring the operating force of a two-part, lever-type electrical connector is provided. In general, the method comprises attaching a tool of the type described above to the external pivots of a lever-type, electrical connector, attaching a catch portion of the tool relative to the connector to displace the lever and produce an electrical signal representing lever force.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION OF THE ILLUSTRATIVE EMBODIMENT

Figure 1:
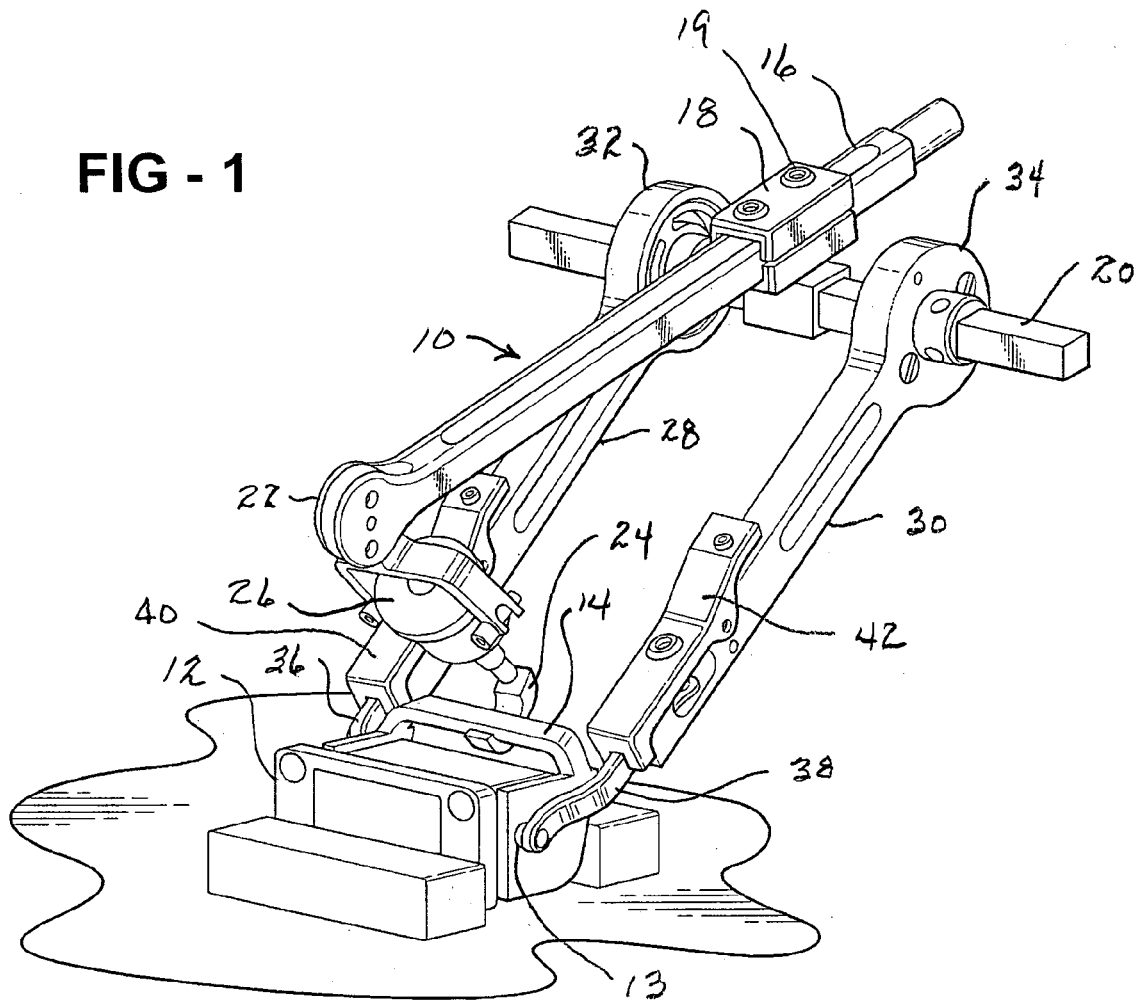
FIG. 1 is a perspective view of a tool made and configured in accordance with the invention and operatively attached to a lever connector.

Referring to the drawings, a universal, configurationally adjustable tool 10 is provided for the purpose of measuring the forces required to mate and/or unmate the two matable components of a lever-type connector 12. The connector 12 has a basket handle shaped lever 14 which can be rotated around exterior pivots 13 on one of the connector parts, as is more fully described in the prior art patents identified above. The two-part electrical connector 12 is placed in a preset condition wherein the two parts are properly aligned and partially engaged. Thereafter, the lever 14 may be rotated around the axis of the pivots 13 to mechanically draw the two parts of the connector 12 together and make multiple parallel electrical circuits therethrough. Rotation of the lever 14 in the opposite direction demates the connector 12 and returns it to the preset condition.

Figure 2:
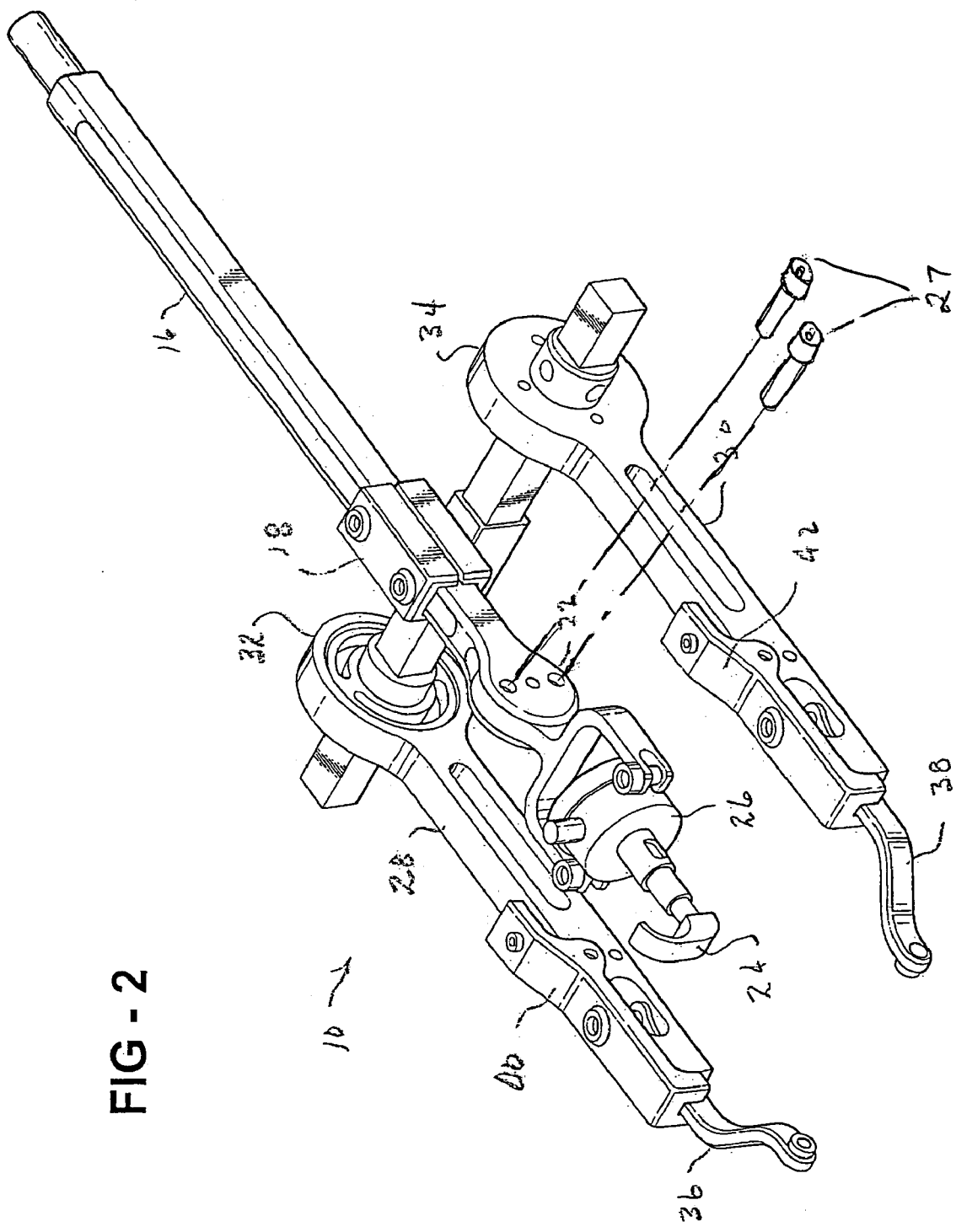
FIG. 2 is a perspective view of the tool in FIG. 1 in a "flat" configuration, usually associated with storage of the tool.

In accordance with the preferred form of the invention, the tool 10 is made largely, for example, of tool steel or stainless steel and comprises the rigid but adjustable combination of an elongate handle 16, the midpoint of which is attached by means of a releasable slide bracket 18 to the midpoint of a base bar 20 having a square cross-section as shown in FIGS. 1 and 2. The term "midpoint" as used herein, includes but is not necessarily limited to an exact center. The slide bracket 18 may be loosened to permit the handle to be moved longitudinally in one direction or the other until the appropriate configuration is achieved and then tightened by means of screws 19. The free end of the handle 16; i.e., the end nearest the connector 12 when the tool 10 is operatively associated therewith, is provided with an angularly adjustable joint 22 connected to a lever attachment means or catch mechanism 24, here in the form of a hook engagable with the lever 14, by way of a load cell device 26. The load cell device 26 is conventional in structure and could, for example, be of the type that uses foil resistor strain gauges (not shown) to produce an electrical signal related to the force transmitted longitudinally therethrough. Using the joint 22, the angle of the load cell axis relative to the longitudinal axis in the handle 16 may be adjusted and fixed in a rigid state by tightening bolts 27.

Reversely similar legs 28 and 30 are attached to the base bar 20 on opposite sides of the handle 16 by means of angularly adjustable joints 32 and 34. Mounted on the free ends of the legs 28 and 30 are inwardly curved adaptor bars 36 and 38 having end cups 44 which are configured to permit attachment of the adaptor bars 36 and 38 to the pivot 13 of the connector 12. Spring biased releases 40 and 42 are mounted on the legs 28 and 30 to permit the adaptor bars 36 and 38 to be swung outwardly for attachment purposes as shown in FIG. 4.

Figure 3:
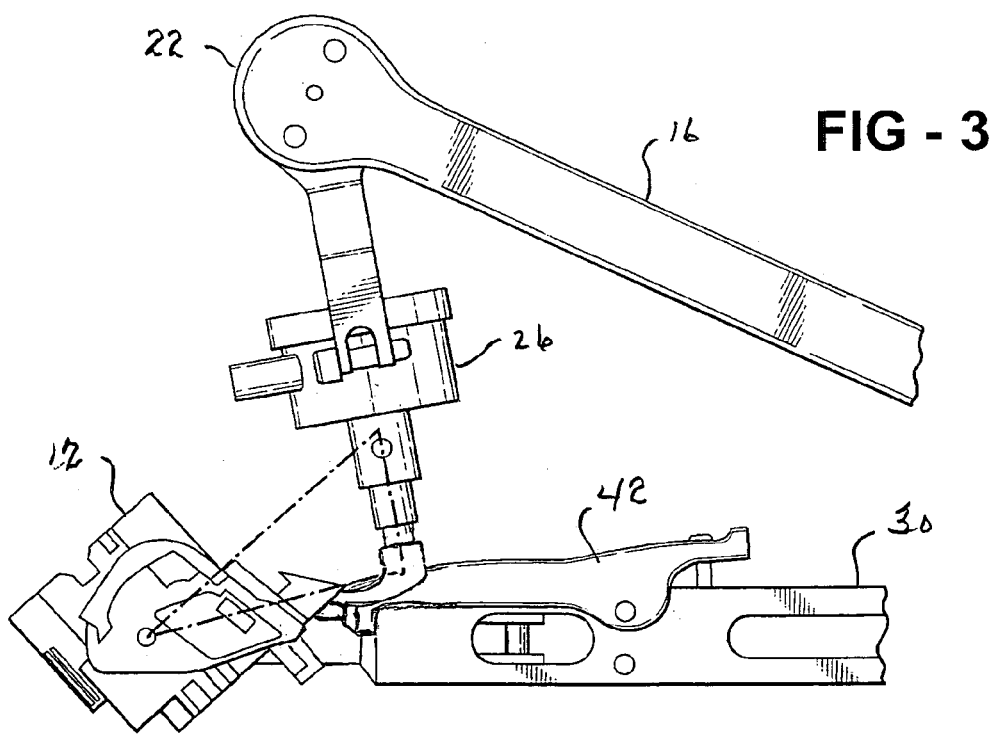
FIG. 3 is a side view of a portion of the tool of FIG. 1 showing the relationship between force vector and mechanical components.

The tool 10 is shown in FIG. 2 in the "straight" or "flat" condition wherein all of the handle 16 and legs 28 and 30 are essentially parallel to one another. This is typically a storage condition; i.e., the joints 22, 32 and 34, along with the slide bracket 18, permit the overall configuration of tool 10 to be changed to accommodate connectors 12 of various sizes and shapes, the overall objective being to configure the tools so that when applied to a mechanically grounded connector 12 as shown in FIG. 1, the force applied to the lever 14 of the connector is tangent to the arc of lever rotation so that the force required to move the lever is correctly represented by the longitudinal strain measured by the load cell device 26. Put another way, the angle between the load cell axis and a line through the pivots 13 and a force input point through the catch mechanism 24 is 90° as shown in FIG. 3. Adjustment is accomplished by loosening the joints 22, 32 and 34 and slide bracket 18 as described above, adjusting the tool 10 into the appropriate configuration and then tightening all of the joints 22, 32 and 34 and/or slide bracket 18. As stated above, tool 10 may alternatively be made in a configurationally fixed form and used only in connection with connectors 12 of constant size and shape.

Figure 4:
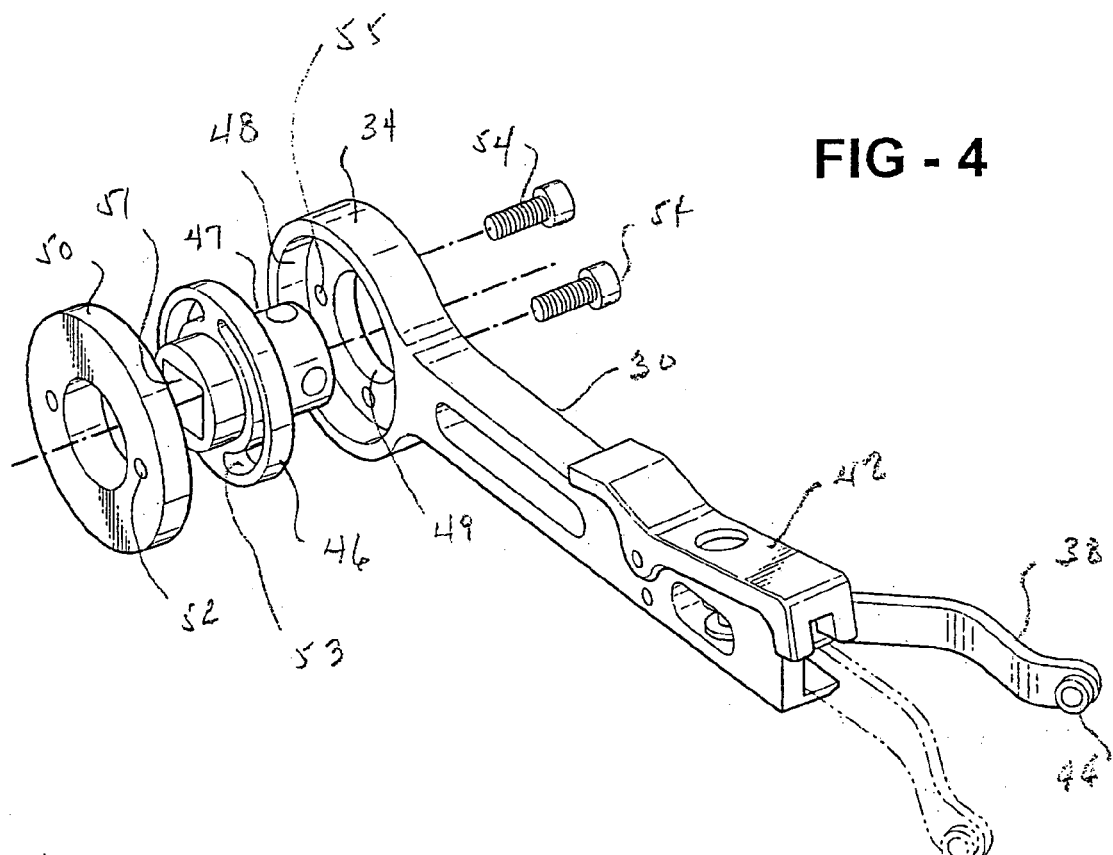
FIG. 4 is an exploded view in perspective of a portion of one of the legs of the tool of FIG. 1.

Referring to FIG. 4, the details of the angularly adjustable joint 34 are shown to comprise a collar 46 having a cylindrical body portion 47 which fits into an aperture 49 such that the collar 46 rests within the recess 48 of the joint 34. A square cross-section bore 51 extends through the collar 46 to allow the collar to be slipped on to the base bar 20 and to maintain an angularly-fixed relationship thereto. The collar 46 has slotted holes 53 to accommodate the threaded portions of screws 54 which pass through holes 55 in the joint body 34. A lock plate 50 fits over the body 47 of the collar 46 and is provided with threaded holes 52 to receive the screws 54. The angular relationship between the arm 30 and the base bar 20, as well as the distance between the legs, may be adjusted by loosening the screws 54, rotating the leg 30 to the desired angular orientation and spacing and thereafter tightened down by driving home the screws 54 in the lock plate 50.

Figure 5:
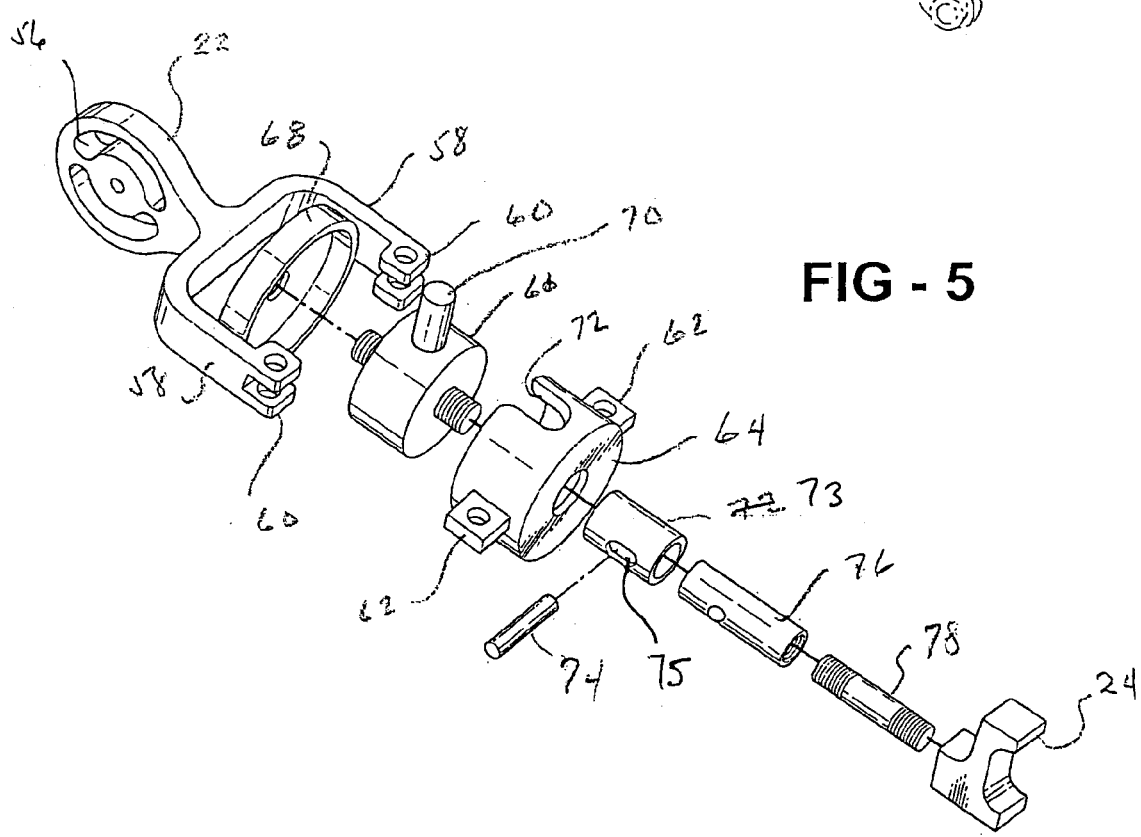
FIG. 5 is an exploded view in perspective of the load cell assembly of the tool of FIG. 1.

FIG. 5 shows the details of the load cell device 26 to comprise the joint 22 having angular holes 56 to permit rotational adjustment by means of the screws shown in FIG. 1. The joint 22 includes a bifurcated bracket with spaced apart parallel legs 58 with end brackets 60 to receive the side tabs 62 of a cap plate 64, which traps the active portion 66 of the load cell between the cap plate 64 and a backer plate 68. A wire 70 extends through the slot 72 in the cap plate 64 and transmits the signal from the load cell device 26. Load cell connector pieces 73, 74, 76 and 78 connect the load cell device 26 to the catch mechanism 24. More specifically, connector piece 73 is an extrusion that is welded to the cap plate 64. Connector piece 76 fits telescopically into extrusion 73 and threads onto active portion 66. Connector piece 74 is a pin that passes through a slot 75 in the extrusion 73 and into a hole in piece 76. The pin 74 is held rigidly in connector piece 76 to prevent rotation of connector piece 76 after it is threaded on the active portion 66.

In practice, the universal tool 10 is adjusted as described above and the cups 44 of the adaptor arms 36 and 38 are securely attached to the pivots 13 of the connector 12. The connector has been previously placed in the "preset" condition wherein the two-part connectors are partially aligned, but not fully mated. The hook-shape catch 24 is attached to the lever 14 and the tool 10, after checking to make sure that all of the slide fittings and joints are fully tightened and that the force vector applied by the load cell device 26 is tangent to the rotation arc of the lever 14, is rotated in the desired direction to either mate or unmate the connector 12. The force transmitted through the active portion to load cell device 26 produces an electrical signal which may be instantly read or recorded or compared to a reference signal to generate an "accept" or "reject" signal and/or to alternatively or simultaneously indicate the actual force required to operate the connector. Assuming a given connector has a standard acceptable force for ergonomic reasons of seventy-five Newtons maximum to rotate the lever into the mated condition, a higher than normal force may indicate improperly manufactured or assembled connectors. Similarly, a lower than normal force may indicate the fact that internal terminals are missing. The tool, when constructed in the universally adjustable form disclosed herein, may be returned to the flat condition shown in FIG. 2 for storage.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A tool for measuring the force required to operate a two-part connector of the type having a lever mounted between two spaced-apart, coaxial pivots on one of the two connector parts, said tool comprising:
    a pair of spaced-apart legs having free ends adapted to be attached to said pivots;
    a catch adapted to engage said lever and exert said force thereon in a direction to cause angular movement of said lever about said pivots;
    a load cell attached to said catch to produce a signal related to the force exerted through said catch; and
    a handle connecting said load cell to said legs
    whereby the movement of said handle and legs about the axis of said pivots swings said lever.

2. A tool as described in claim 1 wherein the angular relationships between said handle, said legs and said catch are such that the force exerted on said lever is substantially tangent to the movement arc of said lever about said pivots.

3. A tool as described in claim 1 wherein the distance between said spaced-apart legs is adjustable to accommodate connectors of different size.

4. A tool as described in claim 1 wherein said catch is a hook.

5. A tool as described in claim 1, further including a base bar connecting said legs to a midpoint of said handle, said legs being attached to said base bar by means of angularly adjustable joints.

6. A tool as described in claim 1, further including adaptor means connected to the free ends of said legs for attachment to the pivots.

7. A universal tool for measuring the force required to operate a two-part connector of the type having a lever mounted between two spaced-apart coaxial pivots on one of the two connector parts, said tool comprising:

a base bar having a longitudinal axis;

a handle having a grip end and a working end and defining a longitudinal axis extending between said grip and working ends;

first means for attaching a midpoint in the handle to a midpoint of the base bar;

a pair of reversely similar legs;

second means for selectively adjustably connecting the legs to the base bar on metrically opposite sides of said midpoint such that the working end of the handle lies between said legs;

a load cell;

third means for selectively angularly adjustably connecting the load cell to the working end of the handle; and a catch attached to said load cell, whereby, by attaching the legs to said pivots and the catch to said lever, angular movement of the grip end of the handle causes angular movement of the lever to operate the connector.

8. A universal tool as described in claim 7 wherein the first means includes a bracket to allow sliding movement of said handle relative to the base bar midpoint.

9. A universal tool as described in claim 7 wherein said second means comprises adjustable rotatable joints, each of said joints including means which may be loosened to enable relative rotation of the legs about the longitudinal axis of the base bar and tightened to maintain the selective angular relationship during use of the tool.

10. A universal tool as described in claim 7 wherein said third means comprises a pivot bracket.

11. A universal tool as described in claim 7 further including an adaptor means mounted on the ends of said legs for attachment to said pivots.

12. A tool as described in claim 11 wherein said adaptors are attached to said legs so as to permit selective outward and inward rotation of said adaptors relative to said legs.

13. A method of measuring the operating force of a two-part lever connector of the type having pivots on one connector part and a swingable lever effective to pull the two connector parts into electronically operative engagement with one another using a tool of the type having legs, a lever catch, a handle attached to the legs, and a load cell attached between the catch and the handle, including the steps of:

(a) attaching the legs of the tool to the pivots of the lever connector;

(b) attaching the catch of the tool to the connector lever; and thereafter (c) moving the tool relative to the connector to swing the lever and to produce from the load cell an electrical signal representing lever operating force.

* * * * *